US00PP37335P2

(12) United States Plant Patent
van Dijk

(10) Patent No.: US PP37,335 P2
(45) Date of Patent: Mar. 17, 2026

(54) ***ANTHURIUM* PLANT NAMED 'AN2181990'**

(50) Latin Name: *Anthurium scherzerianum*
Varietal Denomination: AN2181990

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/315,581

(22) Filed: Aug. 31, 2025

(51) Int. Cl.
*A01H 5/02* (2018.01)
*A01H 6/00* (2018.01)
*A01H 6/10* (2018.01)

(52) U.S. Cl.
USPC ..... Plt./369
CPC ..... *A01H 6/00* (2018.05)

(58) Field of Classification Search
USPC ..... Plt./369
See application file for complete search history.

*Primary Examiner* — Susan Mccormick Ewoldt
(74) *Attorney, Agent, or Firm* — C. Anne Whealy

(57) ABSTRACT

A new and distinct cultivar of *Anthurium* plant named 'AN2181990', characterized by its upright to outwardly arching plant habit; freely clumping growth habit; bushy and dense plants; dark green-colored leaves; freely flowering habit; open inflorescences that are positioned above the foliar plane on strong scapes; ovate to broadly elliptic reddish orange-colored spathes; and reddish orange to red-colored spadices.

2 Drawing Sheets

Figure 1:
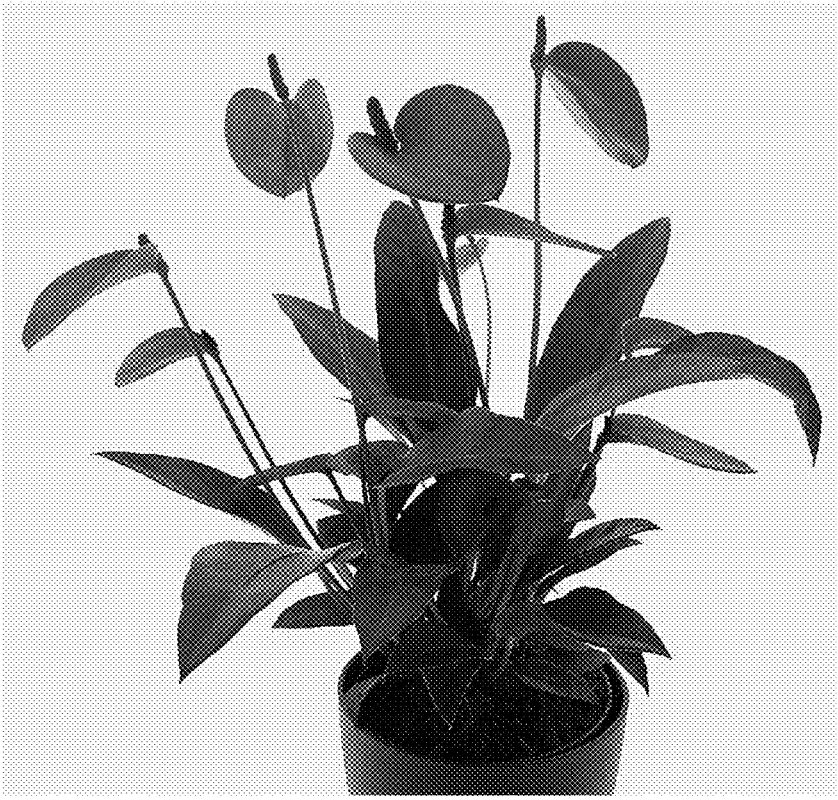

Botanical designation: *Anthurium scherzerianum.*
Cultivar denomination: 'AN2181990'.

CROSS-REFERENCED TO CLOSELY-RELATED APPLICATION

A European Community Plant Breeder's Rights application for the instant plant was filed by the Applicant/Assignee of the instant application, Anthura B.V. of Bleiswijk, The Netherlands on Nov. 20, 2024, application number 2024/2698. Foreign priority is not claimed to this application.

BACKGROUND OF THE INVENTION

The present invention relates to a new and distinct cultivar of *Anthurium* plant, botanically known as *Anthurium scherzerianum*, commonly referred to as Flamingo Flower and hereinafter referred to by the name 'AN2181990'.

The new *Anthurium* plant is a product of a controlled breeding program conducted by the Inventor in Bleiswijk, The Netherlands. The objective of the breeding program is to create new compact *Anthurium* plants with durable red-colored spathes.

The new *Anthurium* plant originated from a cross-pollination made by the Inventor in January 2015 in Bleiswijk, The Netherlands of a proprietary breeding selection of *Anthurium scherzerianum* identified as code number 11-026379-0005, not patented, as the female, or seed, parent with a proprietary breeding selection of *Anthurium scherzerianum* identified as code number 09-023205-0006, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in December 2016.

Asexual reproduction of the new *Anthurium* plant by in vitro meristem propagation in a controlled environment in Bleiswijk, The Netherlands since November 2019 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2181990'. These characteristics in combination distinguish 'AN2181990' as a new and distinct *Anthurium* plant:

1. Upright to outwardly arching plant habit.
2. Freely clumping growth habit; bushy and dense plants.
3. Dark green-colored leaves.
4. Freely flowering habit.
5. Open inflorescences that are positioned above the foliar plane on strong scapes.
6. Ovate to broadly elliptic reddish orange-colored spathes.
7. Reddish orange to red-colored spadices.

Plants of the new *Anthurium* differ primarily from plants of the female parent selection in the following characteristics:

1. Spadices of plants of the new *Anthurium* are shorter than spadices of plants of the female parent selection.
2. Spadices of plants of the new *Anthurium* are straighter than and not as curved as spadices of plants of the female parent selection.

Plants of the new *Anthurium* differ primarily from plants of the male parent selection in the following characteristics:

1. Leaves of plants of the new *Anthurium* are shorter than leaves of plants of the male parent selection.

2. Spadices of plants of the new *Anthurium* are straight whereas spadices of plants of the male parent selection are curled.

Plants of the new *Anthurium* can also be compared to plants of *Anthurium scherzerianum* 'Antarto', not patented. In side-by-side comparisons, plants of the new *Anthurium* differ primarily from plants of 'Antarto' in the following characteristics:

1. Spathes of plants of the new *Anthurium* are narrower than spathes of plants of 'Antarto'.
2. Spadices of plants of the new *Anthurium* are shorter than spadices of plants of 'Antarto'.
3. Spadices of plants of the new *Anthurium* are straight whereas spadices of plants of 'Antarto' are curled.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2181990' grown in a container.

Figure 2:
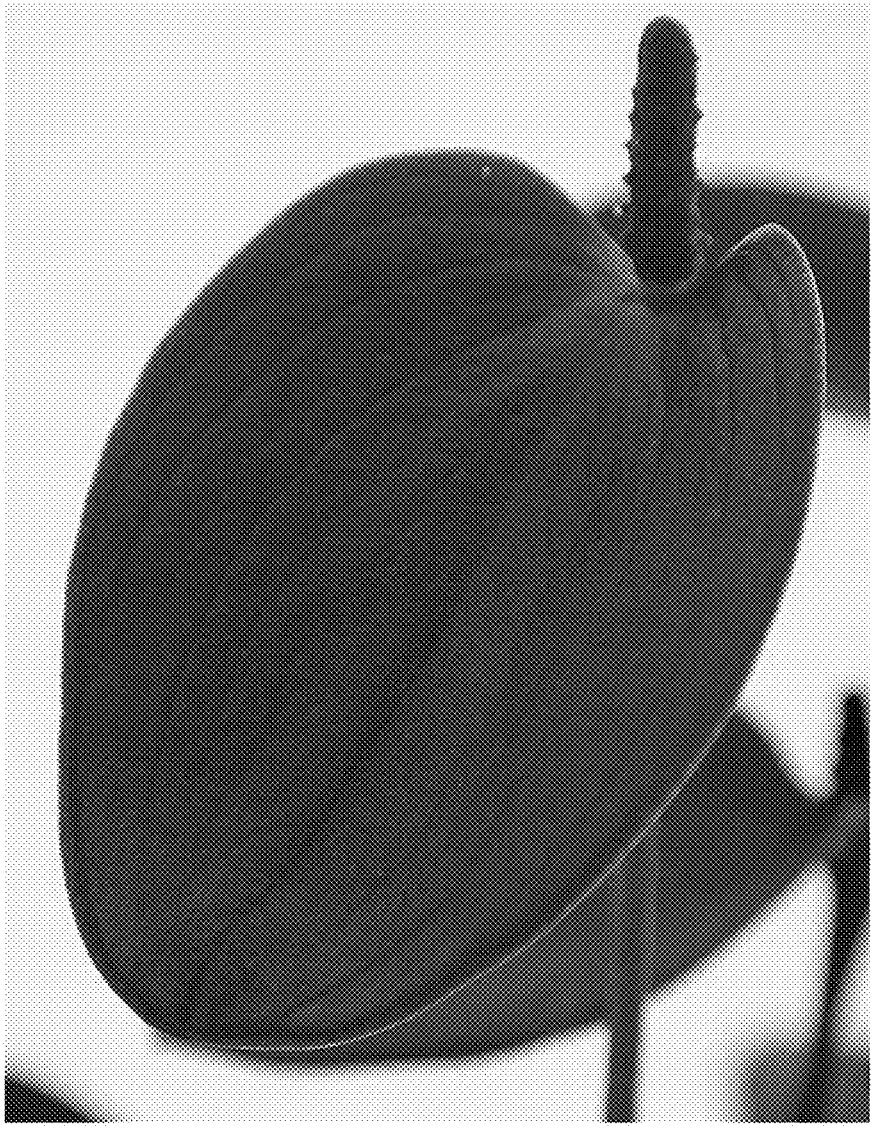

The photograph on the second sheet (FIG. 2) is a close-up view of a typical inflorescence of 'AN2181990'.

DETAILED BOTANICAL DESCRIPTION

The aforementioned photographs and following observations and measurements describe plants grown in 9-cm containers during the winter in a glass-covered greenhouse in Bleiswijk, The Netherlands. Plants were grown under conditions and practices which approximate those generally used in commercial *Anthurium* production. During the production of the plants, day and night temperatures ranged from about 19° C. to about 22.5° C. and light levels ranged from about 100 μmol to about 200 μmol. Plants were nine months from planting young rooted plants when the photographs and the detailed description were taken. In the following description, color references are made to The Royal Horticultural Society Colour Chart, 2015 Edition, except where general terms of ordinary dictionary significance are used.

Botanical classification: *Anthurium scherzerianum* 'AN2181990'.

Parentage:

*Female, or seed, parent*.—Proprietary breeding selection of *Anthurium scherzerianum* identified as code number 11-026379-0005, not patented.

*Male, or pollen, parent*.—Proprietary breeding selection of *Anthurium scherzerianum* identified as code number 09-023205-0006, not patented.

Propagation:

*Type*.—By in vitro meristem propagation.

*Time to initiate roots, summer and winter*.—About two weeks at temperatures ranging from about 19° C. to about 22.5° C.

*Time to produce a rooted young plant, summer and winter*.—About six to eight weeks at temperatures ranging from about 19° C. to about 22.5° C.

*Root description*.—Medium in thickness, fibrous; typically creamy white in color; actual color of the roots is dependent on substrate composition, water quality, fertilizer type and formulation, substrate temperature and physiological age of roots.

*Rooting habit*.—Freely branching, medium density.

Plant description:

*Plant shape*.—Upright to outwardly spreading plant habit; overall shape, broadly ovate to broadly elliptic.

*Growth habit*.—Freely clumping habit imparting a bushy and dense appearance; in a single year of production, about 40 individual plants can be harvested per plant; moderately vigorous growth habit and moderate growth rate.

*Plant height, from soil level to top of leaf plane*.—About 15.4 cm.

*Plant height, from soil level to top of inflorescences*.—About 20.3 cm.

*Plant diameter or spread*.—About 22.8 cm.

Leaf description:

*Arrangement*.—Alternate; simple.

*Length*.—About 9.4 cm.

*Width*.—About 3.5 cm.

*Shape*.—Narrowly ovate to ovate; slightly to strongly carinate.

*Apex*.—Acuminate with a mucronate tip.

*Base*.—Attenuate.

*Margin*.—Entire; not undulate.

*Texture, upper and lower surfaces*.—Smooth, glabrous; moderately coriaceous.

*Venation pattern*.—Pinnate.

*Color*.—Developing leaves, upper surface: Close to 146A; narrow marginal edges, close to 187B. Developing leaves, lower surface: Close to 146D; narrow marginal edges, close to 187B. Fully expanded leaves, upper surface: Close to a blend of 137A and 147A; mucronate apex, close to 185B; venation, close to 144B. Fully expanded leaves, lower surface: Close to 146C; venation, close to 157D.

*Petioles*.—Length: About 4.9 cm. Diameter: Distally, about 2 mm and proximally, about 4 mm. Texture, upper and lower surfaces: Smooth, glabrous. Color, upper surface: Close to 144A to 144C. Color, lower surface: Close to 144B to 144C. Geniculum length: About 8 mm. Geniculum diameter: About 2.5 mm. Geniculum texture, upper and lower surfaces: Smooth, glabrous. Geniculum color, upper surface: Close to 145A. Geniculum color, lower surface: Close to a blend of 145B and 145C. Wing length: About 8.5 mm. Wing diameter: About 3 mm. Wing texture: Smooth, glabrous. Wing color: Close to 144A.

Inflorescence description:

*Inflorescence arrangement and flowering habit*.—Spathes with spadices; open inflorescences held above the foliar plane on strong scapes; flowering structures arise from leaf axils; freely and continuous flowering year-round in controlled temperature greenhouses in The Netherlands; typically about 14 developing and developed inflorescences per plant at one time; inflorescence development commences about 2.5 to 3.5 months after planting rooted young plants.

*Inflorescence longevity*.—On the plant, depending on temperature, spathes maintain good substance for about two months; inflorescences persistent.

*Fragrance*.—None detected.

*Spathes*.—Length: About 5.4 cm. Width: About 4.2 cm. Shape: Ovate to broadly elliptic; slightly concave to slightly convex. Apex: Mucronulate. Base: Cuneate. Margin: Entire. Aspect: About 60° to 110° from the scape axis. Texture, upper and lower surfaces: Smooth, glabrous; moderately coriaceous. Color: When developing, front surface: Close to 41A; mucronulate apex, close to 41C and tinged with close to 144A. When developing, rear surface: Close to a blend of 41B and 41C; mucronulate apex, tinged with close to 164C. Fully developed, front surface: Close to 44C; area adjacent to midvein, tinged with close to between 143A and 148A; with subsequent development, color becomes closer to 146C. Fully developed, rear surface: Close to 39A; area adjacent to midvein, tinged with close to 143A; with subsequent development, color becomes closer to 146C.

*Spadices*.—Length: About 1.5 cm. Diameter: About 4 mm. Shape: Cylindrical, slightly tapering towards the apex; apex, obtuse; base, obtuse; in cross-section, rounded. Aspect: About 55° from the spathe axis and about −5° to 20° from the scape axis. Color: Immature: Close to 33A. Mature: Close to 42A. Flowers: Type: Hermaphroditic. Quantity per spadix: About 45. Height: About 0.5 mm. Diameter: About 2 mm. Shape: Roughly square. Anther color: Close to 42A. Pollen amount: Scarce. Pollen color: Close to 155D. Stigma color: Close to N34A.

*Scapes*.—Length: About 15.4 cm. Diameter: About 2 mm. Strength: Strong, sturdy. Aspect: About 22.5° from vertical. Color: Close to 152B; distally, close to a blend of N34A and 179A.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures of about 30° C. and to be hardy to USDA Hardiness Zone 10.

It is claimed:

1. A new and distinct *Anthurium* plant named 'AN2181990' as herein illustrated and described.

* * * * *